United States Patent [19]
Herron

[11] Patent Number: 6,140,816
[45] Date of Patent: Oct. 31, 2000

[54] METHOD OF DETERMINING THE PERMEABILITY OF SEDIMENTARY STRATA

[75] Inventor: Michael M. Herron, Ridgefield, Conn.

[73] Assignee: Schlumberger Technology Corporation, Ridgefield, Conn.

[21] Appl. No.: 08/989,308

[22] Filed: Dec. 12, 1997

[51] Int. Cl.[7] .................................................. G01V 3/00
[52] U.S. Cl. ............................................ 324/303; 702/12
[58] Field of Search ..................... 702/12, 8; 166/252.5, 166/295; 73/152, 38; 250/405; 324/303

[56] References Cited

PUBLICATIONS

Johnson, D.L., Koplik, J. and Schwartz, L.M., "New Pore–size Parameter Characterizing Transport in Porous Media", Physical Review Letters, (1986), 57, 2564–2567.

Carman, P.C., "Flow of Gases Through Porous Media", (1956), Academic Press–Inc., pp. 12–33.

vanOlphen, H. and Fripiat, J.J., "Data Handbook for Clay Minerals and Other Non–metallic Minerals", Pergamon Press, p. 346.

Herron, M.M. "Permeability Estimation", The Search for Oil & Gas in Latin America & the Caribbean, Schlumberger Surenco C.A., Caracas (1995), 2, 44–45.

Bryant, I. et al, "Bachaquero Bloque IV: A Blessing in Disguise", The Search for Oil & Gas in Latin America & the Caribbean, Schlumberger Surenco C.A., Caracas (1995), 2, 33–61.

Herron, S.L. and Herron, M.M., "Quantitative Lithology: An Application for Open Cased Hole Spectroscopy", Transactions of the 37th Annual Logging Symposium, SPWLA, Paper E, p. 14.

Herron, S.L., Chiaramonte, J.M. and Herron, M.M., "Effect of Modifying Element Mineral Transforms on Geochemical Log Interpretation", Nulcear Geophysics (1994), 8(5), 411–432.

Wendlandt, R.F. and Bhuyan, K., "Estimation of Mineralogy and Lithology from Geochemical Log Measurements", American Association of Petroleum Geologists Bulletin, (1990), 74, 837–856.

D. Marion, A. Nur, and F. Alabert, "Modeling the Relationships Between Sonic Velocity, Porosity, Permeability, and Shaliness in Sand, Shale, and Shaley Sand", SPWLA Thirteenth Annual Logging Symposium, Jun. 11–14, 1989.

Sen, P.N., Straley, C., Kenyon, W.E. and Whittingham, M.S., "Surface–to–Volume Ratio, Charge Density, Nuclear Magnetic Relaxation and Permeability in Clay–Bearing Sandstones", Geophysics,. (1990), 55, 61–69.

(List continued on next page.)

*Primary Examiner*—Christine K. Oda
*Assistant Examiner*—Brij B. Shrivastav
*Attorney, Agent, or Firm*—William B. Batzer; Salzman & Levy

[57] ABSTRACT

A permeability estimator is constructed from the lambda parameter, $\Lambda$, which is the size of dynamically connected pores. For simple pore geometries at high permeabilities, $\Lambda$ should theoretically be proportional to the pore volume-to-surface area ratio. Further, at high permeabilities, the permeability is proportional to $\Lambda^2/F$ where F is the formation factor. Core data are used to establish the proportionality constant. At permeabilities less than about 100 md, the estimated permeability is seen to overestimate the actual permeability by a factor related to the estimate. Thus, a corrected second estimate can be readily made and is shown to match measured permeabilities on a diverse set of sands and shaly sands with a correlation coefficient of 0.89 for log k. The estimate can also be made using NMR relaxation time data with a correlation coefficient of 0.92 for the same data set. The estimate can also be made from mineralogy data where each mineral is assumed to have a fairly constant specific surface area.

20 Claims, 11 Drawing Sheets

OTHER PUBLICATIONS

Nelson, P.H., "Permeability–porosity Relationships in Sedimentary Rocks", Log Analyst, (1994), 35, 38–62.

Bryant, I.D., Baygun, B., Herron, M.M., Mattson, A., Ramamoorthy, R., Stewart, L., Tarig, S.M., Coll, M.C., Cordova, P., Gamero de Villarroel, H., Hernandez, L., Jiminez, Z., Leon, K. and Rondon, L., "Integration of Old and New Measurements to Optimize Redevelopment of the Lower Lagunillas Reservoir of Bloque IV, Lake Maracaibo, Venezuela", paper SPE 36096 Apr. 23–26, 1996.

Bryant, S., Cade, C. and Mellor, D., "Permeability Prediction from Geologic Models", American Association of Petroleum Geologists Bulletin, (1993), 77, 1338–1350.

Kenyon, W.E., "Nuclear Magnetic Resonance as a Petrophysical Measurement", Nucelar Geophysics, (1992), 6, 153–171.

Doyen, P.M., "Permeability, Conductivity, and Pore Geometry of Sandstone", Journal of Geophysical Research, (1988), 93, 7729–7740.

Paterson, M.S., "The Equivalent Channel Model for Permeability and Resistivity in Fluid Saturated Rock–a Re–appraisal", Mechanics of Materials, (1983), 2, 345–351.

Bourbie, T. and Zinszner, B., "Hydraulic and Acoustic Properties as a Function of Porosity in Fountainebleau Sandstone", Journal of Geophysical Research, (1985), 90, 11524–11532.

Katz, A.J. and Thompson, A.H., "Quantitative Prediction of Permeability in Porous Rock", Physical Review B, (1986), 34, 8179–8181.

METHOD OF DETERMINING THE PERMEABILITY OF SEDIMENTARY STRATA

FIELD OF THE INVENTION

The invention relates to well logging procedures and, more particularly, to an improved method of determining the permeability of sedimentary and certain carbonate rock.

BACKGROUND OF THE INVENTION

Over the last several decades, well logging methods have become very sophisticated. Many new procedures, such as Nuclear Magnetic Resonance (NMR), have been used in the testing of well strata. NMR methods have proven useful in determining whether a particular well will be productive, since producible fluids are easily distinguishable by their slow NMR relaxation times.

Estimating permeability of sedimentary formations is one of the most important factors in distinguishing economic from uneconomic reservoirs. Generally, however, the estimation of permeability from log data has been only partially successful. In the past, diversified core data did not clearly correlate with estimated results. It was sometimes difficult to form a straight-line semi-logarithmic plot of permeability as a function of porosity through the data points. Such plots often showed a significant amount of residuals above and below the line.

The present invention introduces an improved method of estimating the permeability of sedimentary rock formations.

The current invention uses nuclear magnetic resonance measurements of the longitudinal or transverse relaxation time constant on the same plug samples used to determine permeability. The equation governing the surface relaxation is combined with a permeability equation using the lambda parameter suggested by Johnson, D. L., Koplik, J. and Schwartz, L. M., "New Pore-size Parameter Characterizing Transport in Porous Media", Physical Review Letters, (1986), 57, 2564–2567. A new, alternate permeability expression is thus provided, having a 0.92 correlation coefficient. The NMR form of the k-Lambda equation appears to be useful, however, only for water-bearing zones, as the values were susceptible to change when hydrocarbon replaces water in the pores.

In an alternate embodiment of the method, the invention then uses a mineral form of k-Lambda. The surface-to-pore volume ratio is expanded into terms relating to the porosity, and to the minerals present. Clay minerals, which contribute most to the surface area of reservoir sands and shaly sands, tend to cluster into fairly unique values of specific surface area. Thus, it was expected that the specific surface area of sediments could be constructed as a linear combination of the mass fractions of the minerals present. The new k-Lambda estimate has a remarkable correlation coefficient of 0.99.

One of the important advantages of the inventive method is that the k-Lambda technique can be activated using log data. The NMR form of the k-Lambda method uses total porosity and magnetic resonance measurements (relaxation times, $T_1$ or $T_2$) data. The mineral form of k-Lambda utilizes total porosity and estimates of the mineral fractions.

Moreover, seismic information can also be incorporated in the inventive method due to well-known correlations among velocity, porosity and clay content, as discussed, for example, in "Modeling the Relationships Between Sonic Velocity, Porosity, Permeability, and Shaliness in Sand, Shale, and Shaley Sand", by D. Marion, A. Nur, and F. Alabert, SPWLA Thirtieth Annual Logging Symposium, Jun. 11–14, 1989.

Another important advantage of the method of this invention is that the k-Lambda technique is a robust means of estimating permeability.

SUMMARY OF THE INVENTION

In accordance with the present invention, there is provided a method of accurately estimating the permeability of sedimentary rock formations from well logging data. The method combines an equation governing the surface relaxation of NMR testing with a permeability equation using the lambda parameter suggested by Johnson et al, to provide a new, alternate permeability expression. The NMR form of the k-Lambda method uses total porosity and magnetic resonance measurements (relaxation times, $T_1$ or $T_2$) data. In an alternate embodiment, the method provides an estimate using a mineral form of k-Lambda. The surface-to-pore volume ratio is expanded into terms relating to the porosity and terms relating to the minerals present.

It is an object of this invention to provide an improved method of estimating the permeability of sedimentary rock.

It is another object of the invention to provide a technique of determining permeability of sedimentary formations by combining the equation governing NMR relaxivity with the k-Lambda permeability equation.

It is still another object of this invention to provide a technique of determining permeability from well logging data by combining the equation governing NMR relaxivity with the mineral form of the k-Lambda permeability equation.

BRIEF DESCRIPTION OF THE DRAWINGS

A complete understanding of the present invention may be obtained by reference to the accompanying drawings, when considered in conjunction with the subsequent detailed description, in which.

DESCRIPTION OF THE PREFERRED EMBODIMENT

Generally speaking, the invention features a method of accurately estimating the permeability of sedimentary rock formations from well logging data. The method combines an equation governing the surface relaxation of NMR testing with a permeability equation using the lambda parameter suggested by Johnson et al, to provide a new, alternate permeability expression having a 0.92 correlation coefficient. The NMR form of the k-Lambda method uses total porosity and magnetic resonant measurements (relaxation times, $T_1$ or $T_2$) data. The invention also provides an estimate using a mineral form of k-Lambda. The surface-to-pore volume ratio is expanded into terms relating to the porosity and terms relating to the minerals present. The new k-Lambda estimate has a remarkable correlation coefficient of 0.99.

Figure 1:
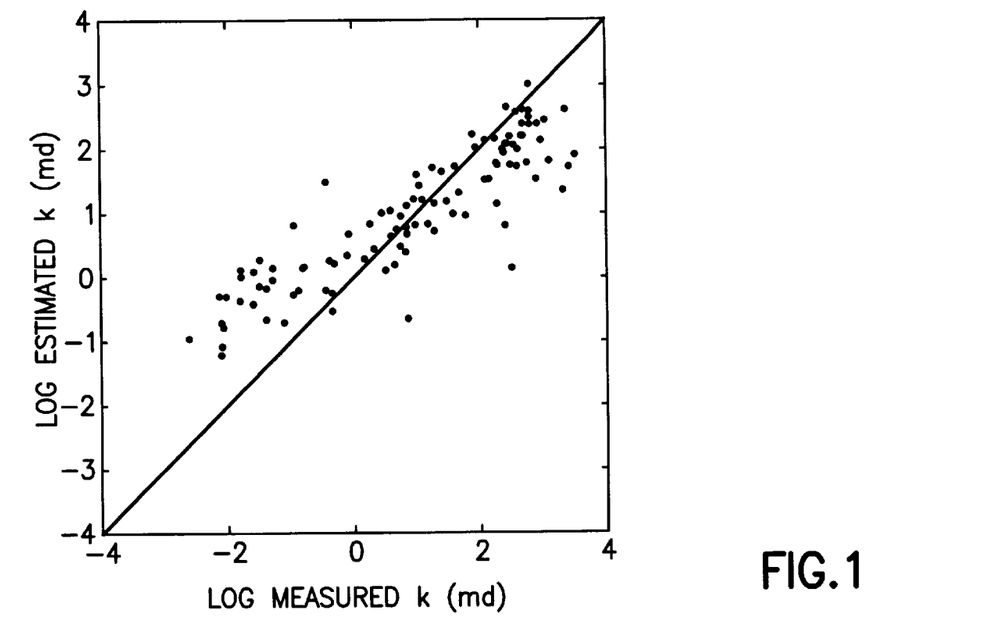
FIG. 1 illustrates a logarithmic graphic plot of measured permeability against an estimate with optimized prefactor $Z_1$ using data of Sen, P. N., Straley, C., Kenyon, W. E. and Whittingham, M. S., "Surface-to-Volume Ratio, Charge Density, Nuclear Magnetic Relaxation and Permeability in Clay-Bearing Sandstones", Geophysics, (1990), 55, 61–69.
Figure 1A:
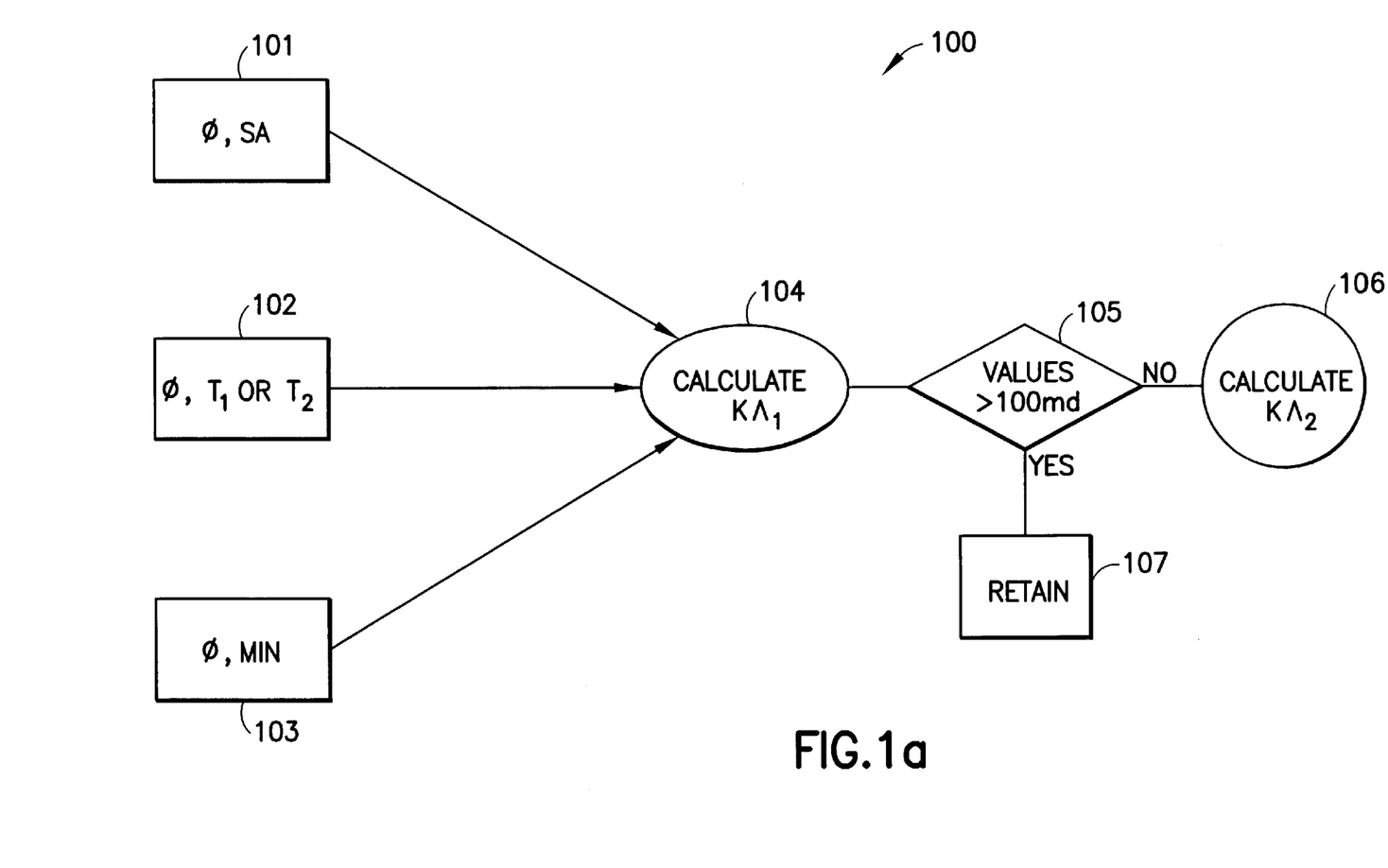
FIG. 1a depicts a flow diagram showing the method of this invention.

Now referring to FIG. 1a, a flow chart 100 depicts the method of this invention. The method comprises obtaining core data for a rock formation by one of several techniques, such as by pore size measurements (step 101); by measuring $T_1$ and $T_2$ by NMR techniques (step 102); and by obtaining mineral data (step 103). For any one of these data values obtained in steps 101, 102, and 103, respectively, a first k-Lambda expression is obtained (step 104). Thereafter, the decision block 105 is entered, wherein all k-Lambda values above a given threshold are retained (step 107), and those falling below the given threshold, such as 100 millidarcies, are discarded, and a second k-Lambda expression is calculated in its place (step 106).

Moreover, seismic information can also be incorporated in the inventive method due to well-known correlations among velocity, porosity and clay content, as discussed, for example, in "Modeling the Relationships Between Sonic Velocity, Porosity, Permeability, and Shaliness in Sand, Shale, and Shaley Sand", by D. Marion, A. Nur, and F. Alabert, SPWLA Thirtieth Annual Logging Symposium, Jun. 11–14, 1989.

The recent method, suggested by Johnson, introduced the lambda parameter, $\Lambda$, as the size of dynamically connected pores and suggested that, for certain simple pore geometries, the permeability should be related to $\Lambda$ and Archie's formation factor, $F$, as shown in Equation (1), below:

$$k = \frac{8\Lambda^2}{F} \tag{1}$$

The term $\phi^{m^*}$ can be substituted for $1/F$ to give:

$$k \quad \Lambda^2 \phi^{m^*} \tag{2}$$

Despite $\Lambda$ being difficult to measure, in those same simple pore geometries, $\Lambda$ should be inversely proportional to the surface area-to-pore volume ratio, Equation (3).

$$\frac{1}{\Lambda} \propto \frac{S}{V_P} \tag{3}$$

This leads to an expression for a permeability estimate, $k_{\Lambda 1}$, which needs only a proportionality constant, $Z_1$:

$$k_{\Lambda 1} = \frac{Z_1 \phi^{m^*}}{\left(\frac{S}{V_P}\right)^2} \tag{4}$$

Equation (4) is another expression of the Kozeny-Carman equation, as described in Carman, P. C., "Flow of Gases Through Porous Media", (1956), Academic Press Inc., p. 182; and Nelson, P. H., "Permeability-porosity Relationships in Sedimentary Rocks", Log Analyst, (1994), 35, 38–62. Also, Equation (2) is similar to the expression disclosed in Katz, A. J. and Thompson, A. H., "Quantitative Prediction of Permeability in Porous Rock", Physical Review B, (1986), 34, 8179–8181, with the critical length $l_c$ replacing A. Equation (2) is also similar to the relationship shown by Paterson, M. S., "The Equivalent Channel Model for Permeability and Resistivity in Fluid Saturated Rock—a Re-appraisal", Mechanics of Materials, (1983), 2, 345–351; with effective hydraulic radius replacing A. Many other, similar equations are extant.

The diversified core data of Sen et al include measurements of porosity, formation factor, specific surface area, matrix density—which is used to convert specific surface area to surface-to-pore volume, and permeability on samples from many geological formations and geographical locations. Use of these data to solve for the regression coefficient leads to a value of $Z_1=88$.

Referring to FIG. 1, the regression results are shown. Clearly, there are significant residuals above and below the line at high and low permeabilities. These residuals cannot be addressed without altering the form of the equation. This has led in the past to the use of higher exponents for the porosity term (see Nelson reference cited above).

The initial $k_{A1}$ estimate of permeability from Equation (4) should be most applicable in the simplest pore systems at relatively high permeabilities.

Figure 2:
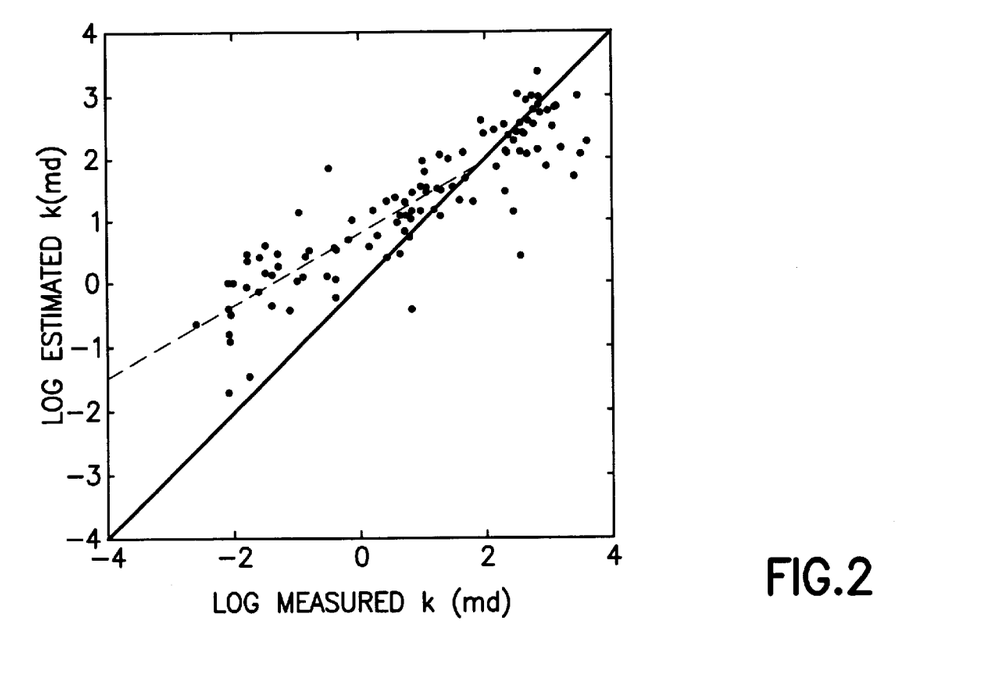
FIG. 2 depicts a logarithmic graphic plot of measured permeability against the first portion of the k-Lambda estimate (Equation (7), using an increased prefactor, $Z_1$.

Referring to FIG. 2, the estimate agrees with the measured permeability at the highest levels, if $Z_1$ is increased to 200. Now it can be seen that the estimate is too high for samples with permeabilities below about 100 md (1 millidarcy=$10^{-11}$ cm$^2$) and that the degree of overestimation is roughly proportional to the difference between the logarithm of the estimate and 2.0. The bias is due to the difference between the true hydraulic radius and that estimated simply from the $V_p/S$ ratio. Doyen, P. M., "Permeability, Conductivity, and Pore Geometry of Sandstone", Journal of Geophysical Research, (1988), 93, 7729–7740; and Bryant, S., Cade, C. and Mellor, D., "Permeability Prediction from Geologic Models", American Association of Petroleum Geologists Bulletin, (1993), 77, 1338–1350; have reported that pore blocking in simple pore systems becomes important at around 10% porosity and below. In these more complicated samples, the effect of pore blocking appears to become pronounced at 100 md permeability. Fortunately, it appears that the bias can be modeled as a regular deviation between the logarithm of the measured permeability and the estimate. Thus, a correction can be made.

The dashed line shown in FIG. 2, representing permeabilities less than 100 md, can be represented by equation (5):

$$k_{A2} = \frac{Z_2 \phi^{1.7m^*}}{\left(\frac{S}{V_p}\right)^{3.4}} \tag{5}$$

The constant $Z_2$ is equal to $0.37Z_1^{1.7}$. Together, Equations (4) and (5) represent an accurate and broadly applicable means of estimating permeability. The $k_{A1}$ estimate holds for values greater than 100 millidarcies. When $k_{A1}$ is less than 100 md, the $k_{A2}$ estimate compensates for the $k_{A1}$ overestimation. Equations (4) and (5) represent the surface-to-pore volume form of the k-Lambda expression.

Figure 3:
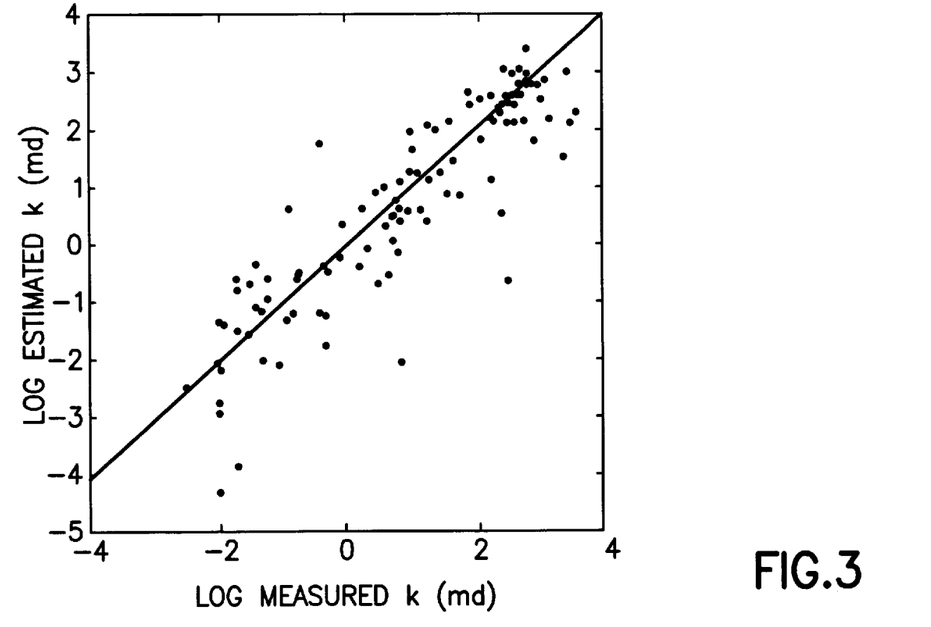
FIG. 3 shows a logarithmic graphic plot of measured permeability against the complete k-Lambda estimate (Equations 7, 8), using the data of FIG. 1.

Referring to FIG. 3, the combination of the $k_{A1}$ estimate Equation (4) and the $k_{A2}$ estimate Equation (5) produces a reasonably accurate means of approximating the permeability of the Sen et al samples using measured porosity, m* and $S/V_p$. As a caution, note that the measurement of specific surface area on those samples involved use of a small aliquot adjacent to the permeability plug. Any sample heterogeneity will introduce some noise in the apparent agreement between k-Lambda and the measured permeability.

Fortunately, nuclear magnetic resonance measurements of $T_1$, the longitudinal relaxation time constant, were also reported by Sen et al. These measurements were made on the same plug samples used to determine permeability. The surface-to-pore volume ratio can be related to the $T_1$ value by Equation (6), which assumes the fast diffusion limit, through ρ, the surface relaxivity, as reported by Kenyon, W. E., "Nuclear Magnetic Resonance as a Petrophysical Measurement", Nuclear Geophysics, (1992), 6, 153–171.

$$\frac{1}{T_1} \rho \left(\frac{S}{V_p}\right) \tag{6}$$

Equations (4) and (6) can then be combined into an alternate expression of the $k_{A1}$ estimate:

$$k_{A1} = Z_3 \phi^{m^*} T_1^2 \tag{7}$$

Although $T_1$ has been used in the above example, $T_2$ can be used instead of $T_1$.

Figure 4:
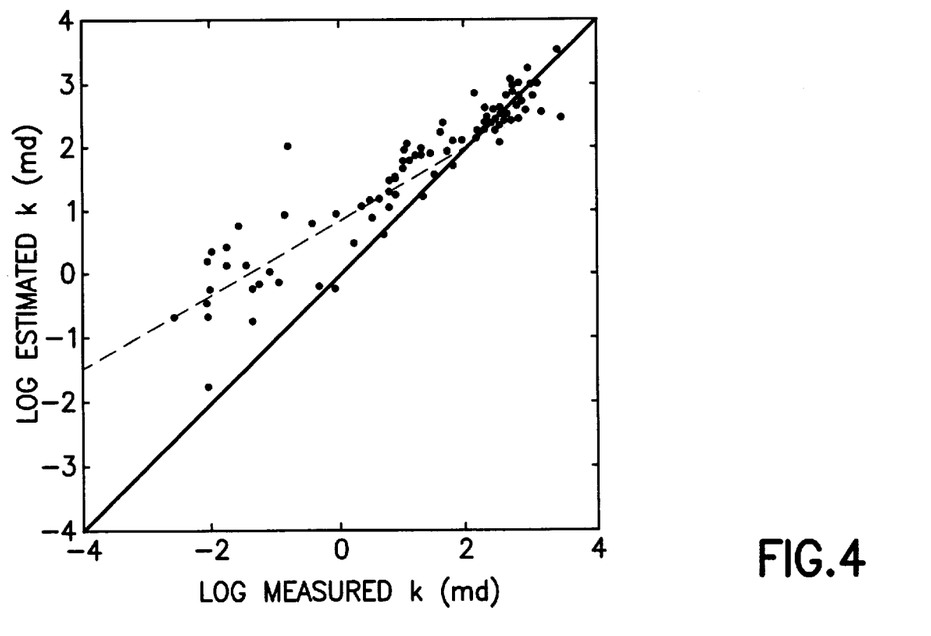
FIG. 4 illustrates a logarithmic graphic plot of permeability values using the Sen et al. Tl NMR data and estimate values in accordance with the first portion of the k-Lambda estimate (Equation 7)

Referring to FIG. 4, there is shown a comparison between the logarithm of measured permeability and permeability derived from porosity, m*, and $T_1$ from the data of Sen et al using Equation (7) and a value of $Z_3=0.1$, where $T_1$ is in milliseconds. As in FIG. 2, the data below about log k=2 (100 md) show that the initial estimate of $k_{A1}$ is too large by an amount about proportional to the difference between 2.0 and the logarithm of the $k_{A1}$ estimate. The dashed line illustrated in FIG. 4 is identical to that depicted in FIG. 2. The second k-Lambda estimate is provided by equation 8:

$$k_{A2} = Z_4 \phi^{1.7m^*} T_1^{3.4} \tag{8}$$

Figure 5:
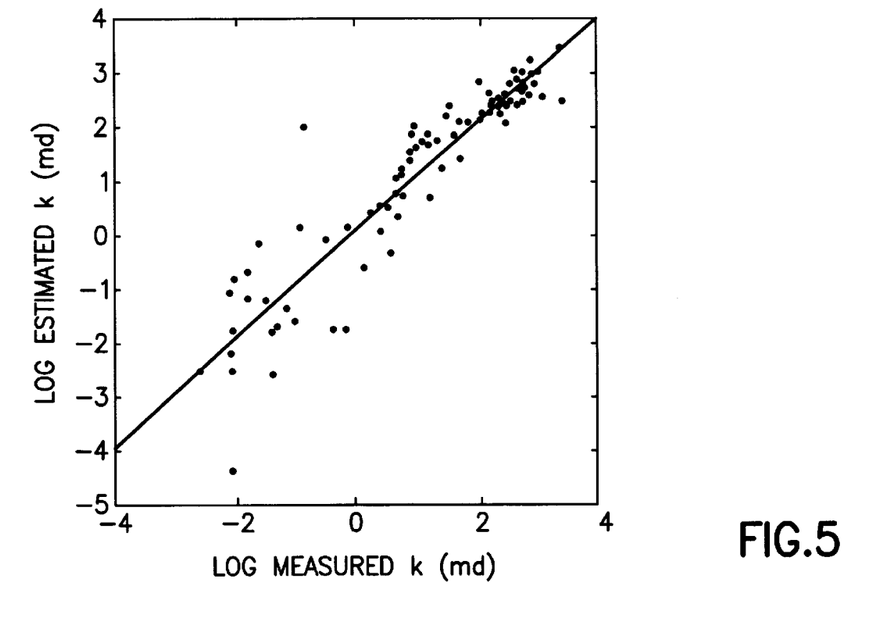
FIG. 5 depicts a logarithmic graphic plot of measured permeability versus the logarithm of the complete k-Lambda estimate.

Referring now to FIG. 5, the two permeability estimates are combined, one for estimates above 100 md, and one for estimates less than 100 md. This combination produces the overall k-Lambda estimate which agrees well with the measured permeabilities, as shown in FIG. 5. The correlation coefficient between the logarithms of permeability is 0.92. Equations (7) and (8) represent an NMR form of the k-Lambda estimate.

The better level of agreement between the measured permeabilities and the NMR form of the k-Lambda expression, compared to the surface-to-pore volume form, may reflect some of the core sample heterogeneties referred to above. The NMR form of the k-Lambda equation could be used in NMR logging provided an accurate total porosity is available. However, the mean $T_1$ or $T_2$ value may be useful only in a water-bearing zone, as these values are susceptible to a change when hydrocarbon replaces water. A better answer will rely on the fact that the short $T_2$ values are most reflective of the high specific surface area and at the same time are virtually independent of the fluid in the coarse pores.

An alternative, mineral form of k-Lambda may have the greatest potential use in the oilfield. The surface-to-pore volume ratio can be expanded into terms relating to the porosity and terms relating to the minerals present. In Equation (9), $S_0$ is the specific surface area as typically measured in m$^2$/g units and $\rho_m$ is the matrix density. These are porosity independent variables.

$$\frac{S}{V_p} = S_0 \rho_m \frac{1-\phi}{\phi} \tag{9}$$

Clay minerals contribute most to the surface area of reservoir sands and shaly sands. The specific surface area of different clay minerals tends to cluster into fairly unique values, as reported by vanOlphen, H. and Fripiat, J. J., "Data Handbook for Clay Minerals and Other Non-metallic Minerals", Pergamon Press, p. 346. Thus, it might be expected that the specific surface area of sediments could be constructed as a linear combination of the mass fractions of the minerals present:

$$S_0 = \Sigma M_i S_0 \quad (10)$$

It would be most important that equation (10) hold for the clay minerals, because of their contribution to surface area. Wendlandt and Bhuyan showed that the specific surface area of Utah sands and shaly sands was essentially a linear combination of the clays kaolinite, illite, and smectite present in the rocks. Data are less clear for non-clay minerals but the data of Sen et al can provide some insight. The minimum So value in that data set is 0.22 m²/g for a medium-grained sandstone and might be thought of as corresponding to the most quartz-rich sandstones. Interestingly, the specific surface area of medium grain (200 mm diameter) spheres would be only about 0.011 m²/g. This suggests that most of the specific surface area probed in the BET $N_2$ adsorption technique is due to surface imperfections rather than to particle size.

form of the $k_{A1}$ estimate using the same $Z_1$ as in equation (4):

$$k_{A1} = \frac{Z_1 \phi^{m^*+2}}{\rho_m^2 (1-\phi)^2 (\sum M_i S_{0i})^2} \quad (11)$$

The applicability of Equation (11) is seen first for a set of Fontainebleau formation samples with essentially no minerals present other than quartz. Porosity and permeability values for the Fontainebleau quartz arenites are shown in a semilogarithmic plot in FIG. 6. Note that these data do not exhibit the common linear relationship in such a plot.

It is assumed that the specific surface area of the quartz grains is 0.22 m²/g. Using a matrix density of 2.65 g/cm³, Equation (11) can give the $K_{A1}$ permeability estimation. The value of m* can be estimated from Equation (12):

$$m^* = 1.653 + 0.0818(S_0 \rho_g)^{0.5} \quad (12)$$

which is derived from the data of Sen et al for those samples where a value of m* was actually measured rather than assumed to be equal to 2. The coefficients in Equation (12) were determined from a least squares optimization. The correlation coefficient for 79 samples is only 0.55, but the standard error of the estimate is 0.1, which is sufficiently precise for the permeability estimate.

Figure 7:
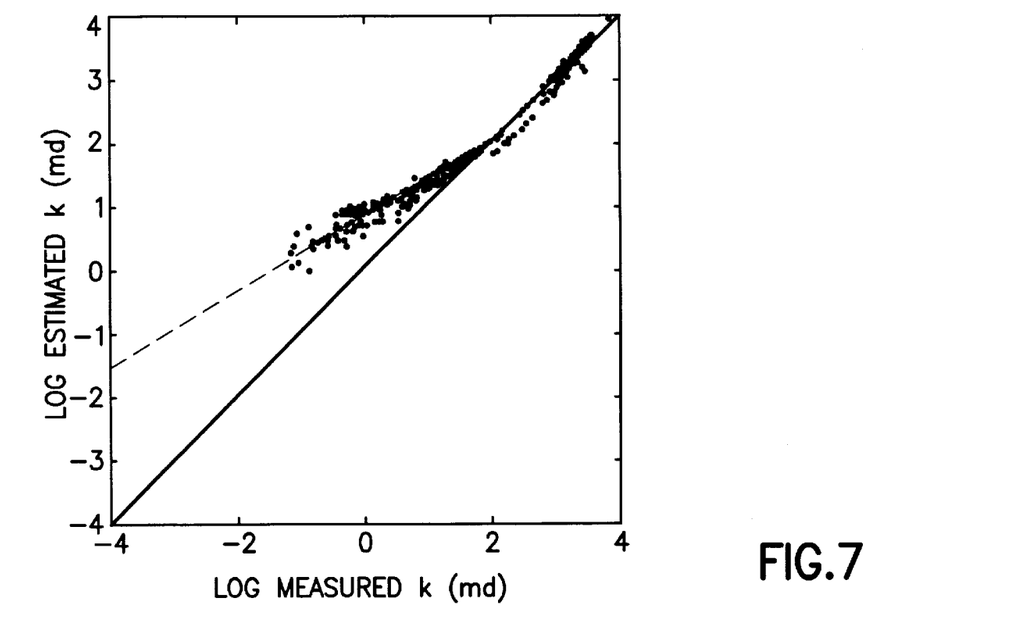
FIG. 7 illustrates a logarithm plot of measured permeability and values estimated from the first portion of the mineral form of the k-Lambda equation (Equation (11))

Referring to FIG. 7, a logarithm of the measured permeability of the Fontainebleau samples is compared with the $k_{A1}$ estimate from Equation (11). As was seen in FIGS. 2 and 4, the estimated permeability agrees well with measured permeability for values above about 100 md. Below that value, the $k_{Ad1}$ estimate regularly overestimates the permeability. The dashed line is the same as shown in FIGS. 2 and 4.

A $k_{A2}$ expression can be derived for the mineral form of the k-Lambda equation, Equation (13). The coefficient $Z_2$ is the same as in Equation (5):

$$k_{A2} = \frac{Z_2 \phi^{1.7(m^*+2)}}{\rho_M^{3.4}(1\phi)^{3.4}(\sum M_i S_{0i})^{3.4}} \quad (13)$$

Figure 8:
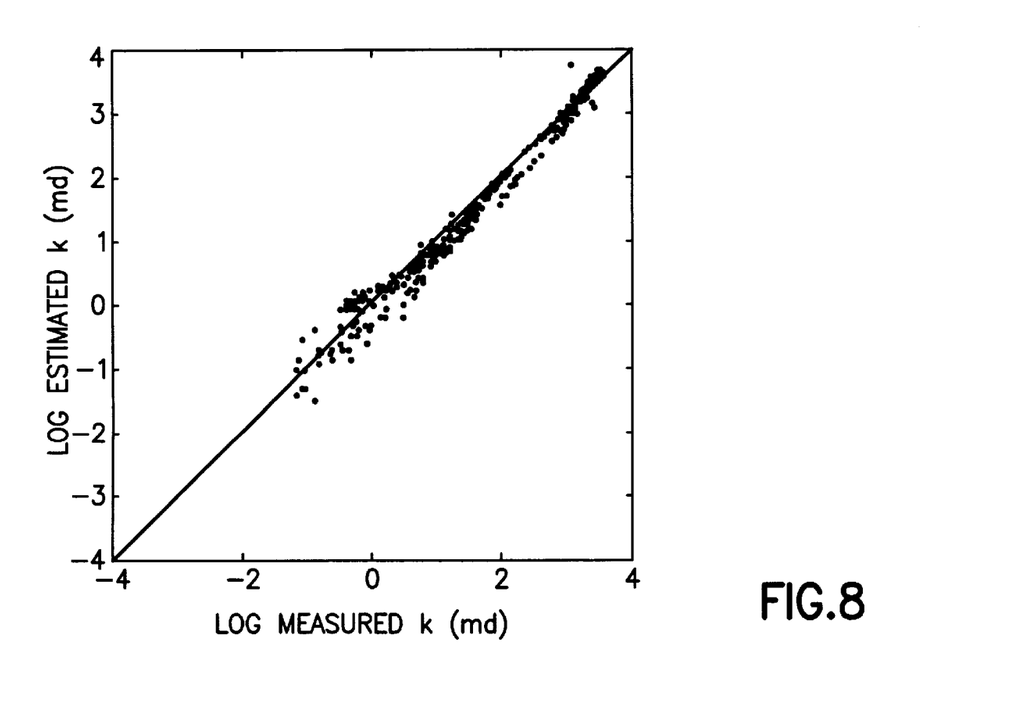
FIG. 8 depicts a logarithmic plot of measured permeability against the logarithm of the complete k-Lambda estimate (Equations 11, 12) using porosity data of Bourbie and Zinszner.

Referring now to FIG. 8, a comparison is made between the logarithms of measured permeability of the K-lambda estimate from Equations (11) and (13). The agreement is remarkable: a correlation coefficient of 0.99. Considering the assumption of a constant m* and constant $S_0$ over the entire data set, the level of agreement is especially remarkable.

Figure 6:
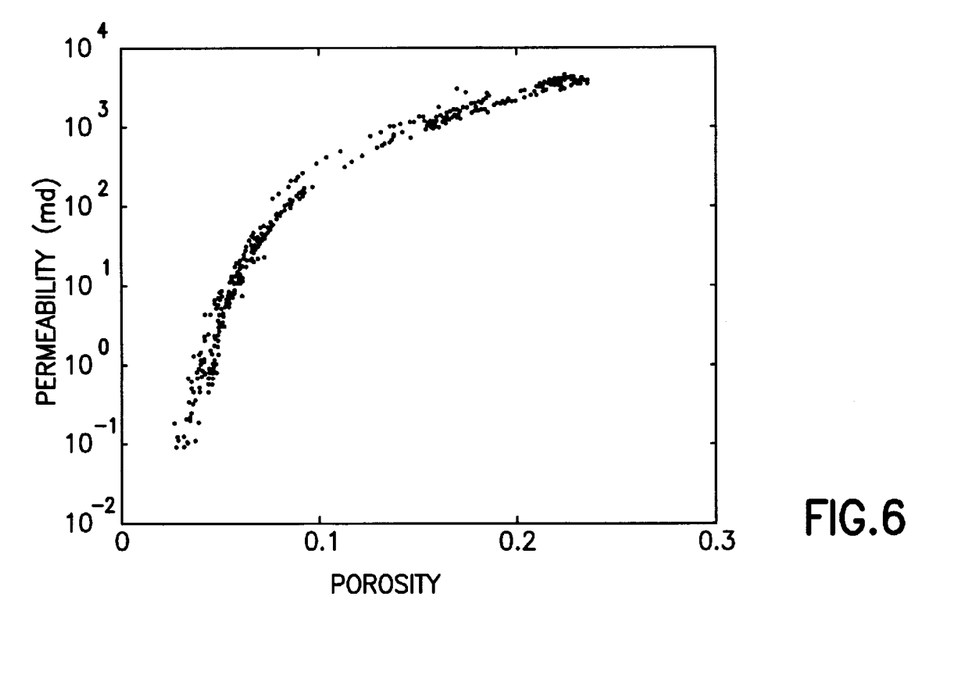
FIG. 6 shows a plot of porosity and permeability values for the clay-free Fontainebleau formation quartz arenites, described in Bourbie, T. and Zinszner, B., "Hydraulic and Acoustic Properties as a Function of Porosity in Fontainebleau Sandstone", Journal of Geophysical Research, (1985), 90, 11524–11532.
Figure 9:
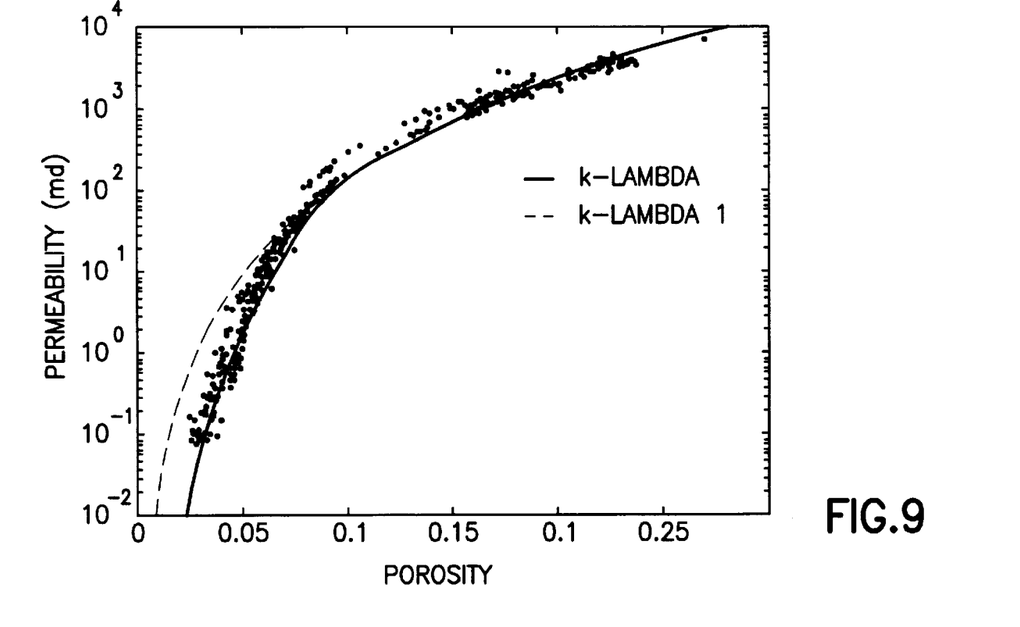
FIG. 9 shows a semi-logarithmic plot of core porosity vs. core permeability values and k-Lambda permeability estimates for the clay-free Fontainebleau formation quartz arenites.

The semilogarithmic plot of the porosity and permeability data in FIG. 6 showed that the Fontainebleau sandstones do not exhibit the commonly observed linear relationship in such a plot. It is interesting to overlay the core data with the clay-free predictions of the k-Lambda and $k_{A1}$ permeability estimates (FIG. 9). Here it can be seen that the non-linear form of this poroperm plot is expected from the k-Lambda equation, provided that the mineralogy is constant.

FIG. 8 compares the logarithms of measured permeability and the k-Lambda estimate from Equations (11) and (13). The correlation coefficient is 0.99. Once again, considering the assumption of a constant m* and constant $S_0$ over the entire data set, the level of agreement is remarkable.

In the work of Herron, M. M., "Permeability Estimation", The Search for Oil & Gas in Latin America & the Caribbean, Schlumberger Surenco C. A., Caracas (1995), 2, 44–45, and Bryant, I. et al, "Bachaquero Bloque IV: A Blessing in Disguise", The Search for Oil & Gas in Latin America & the Caribbean, Schlumberger Surenco C. A., Caracas (1995), 2, 33–61,equation (11) has been modified to account for the fact that apparently not all of the surface area of platy clay minerals participates in hydraulic flow, or is probed by the BET technique. A $v_i$ factor was introduced. That is the fraction of the total surface area of a given mineral that affects fluid flow (Equation (14). A value of $v_i=0.1$ is appropriate for detrital clay minerals.

$$S_0 = \Sigma M_i v_i S_0 \quad (14)$$

This makes the mineral form of the $k_{A1}$ estimate:

$$k_{A1} = \frac{Z_1 \phi^{m^*+2}}{\rho_M^2 (1\phi)^2 (\sum M_i v_i S_{0i})^2} \quad (15)$$

Figure 10:
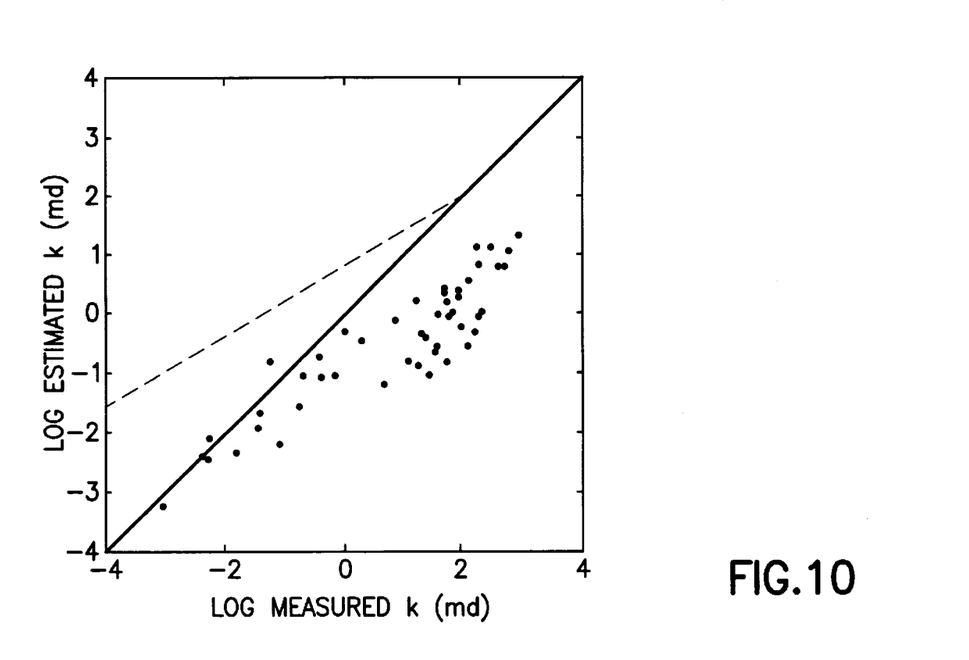
FIG. 10 illustrates a logarithmic plot of measured permeability versus the logarithm of the first portion of the k-Lambda estimate (Equation 15) using mineralogy data of Wendlandt, R. F. and Bhuyan, K., "Estimation of Mineralogy and Lithology from Geochemical Log Measurements", American Association of Petroleum Geologists Bulletin, (1990), 74, 837–856; with a $v_i$ value of 1.

Referring to FIG. 10, it is clear that the introduction of the $v_i$ coefficient is necessary. The $k_{A1}$ estimate of permeability of the Utah sands and shales of Wendlandt and Bhuyan has been made using Equation (15) and the specific surface areas given in Table 1, below. A value of $v_i=1$ was taken for all minerals. The value of m* was taken from Equation (12). It can be seen that the $k_{A1}$ estimate greatly underestimates the permeabilities of all but the shaliest samples.

TABLE 1

| Mineral | Specific Surface Area (m²/g) |
|---|---|
| Kaolinite | 23* |
| Illite | 101* |
| Smectite | 94* |
| Quartz | 0.22 |
| Na-Feldspar | 0.3 |
| K-Feldspar | 0.3 |
| Pyrite | 0.3 |

TABLE 1-continued

| Mineral | Specific Surface Area (m²/g) |
|---|---|
| olomite | 2 |
| Siderite | 2 |
| Ankerite | 2 |

*vanOlphen, H. and Fripiat, J. J., "Data Handbook for Clay Minerals and Other Non-metallic Minerals", Pergamon Press, p. 346.

The values in Table 1are of specific surface areas used for the estimation of permeability in the Utah samples. Applicable values for feldspars, pyrite and carbonate minerals need refinement.

Figure 11:
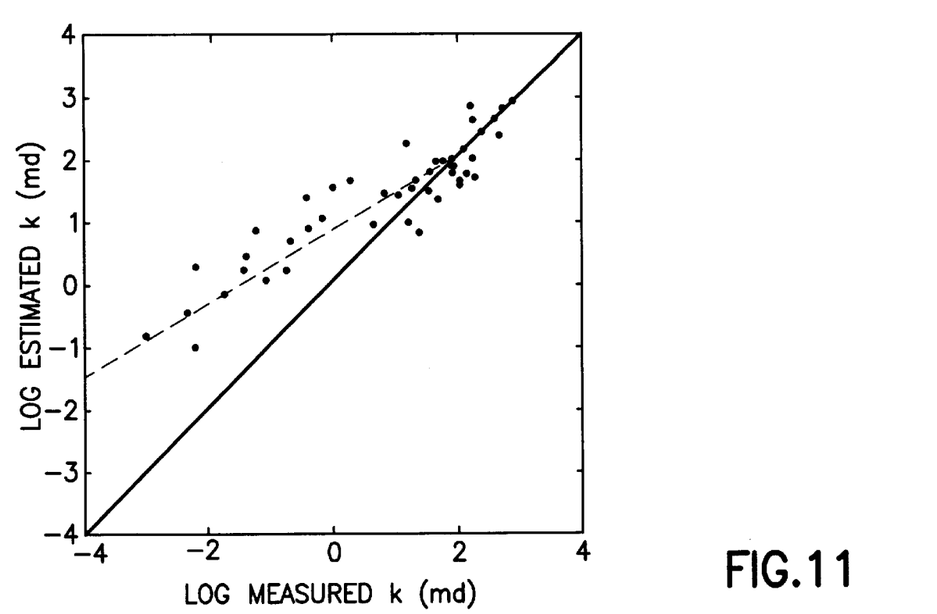
FIG. 11 depicts a logarithm plot of measured permeability versus the logarithm of the first portion of the k-Lambda estimate (Equation 15) using the mineralogy data of Wendlandt and Bhuyan with a $v_i$ value of 0.1 for clays.

In FIG. 11, the $v_i$ values of the clay minerals are set to 0.1, while those of the other minerals remain at 1.0. With this adjustment, the $k_{A1}$ estimate agrees with the measured permeabilities in the highest permeability samples. The estimated permeability regularly overestimates the actual permeability in the same manner seen in FIGS. 2, 4 and 7. The value of $v_i$=0.1 for clays appears to be approximately valid for most detrital clays. However, for authigenic clays, such as the platy illite in the Irish Sea, more of the clay surface area influences fluid flow; values of $v_i$=0.2 are found to be suitable.

Again, the $k_{A2}$ estimate can be constructed from $k_{A1}$ (Equation (15) and the dashed line in FIG. 11:

$$k_{A2} = \frac{Z_2 \phi^{1.7(m^*+2)}}{\rho_M^{3.4}(1\phi)^{3.4}(\sum M_i v_i S_{0i})^{3.4}} \quad (16)$$

Figure 12:
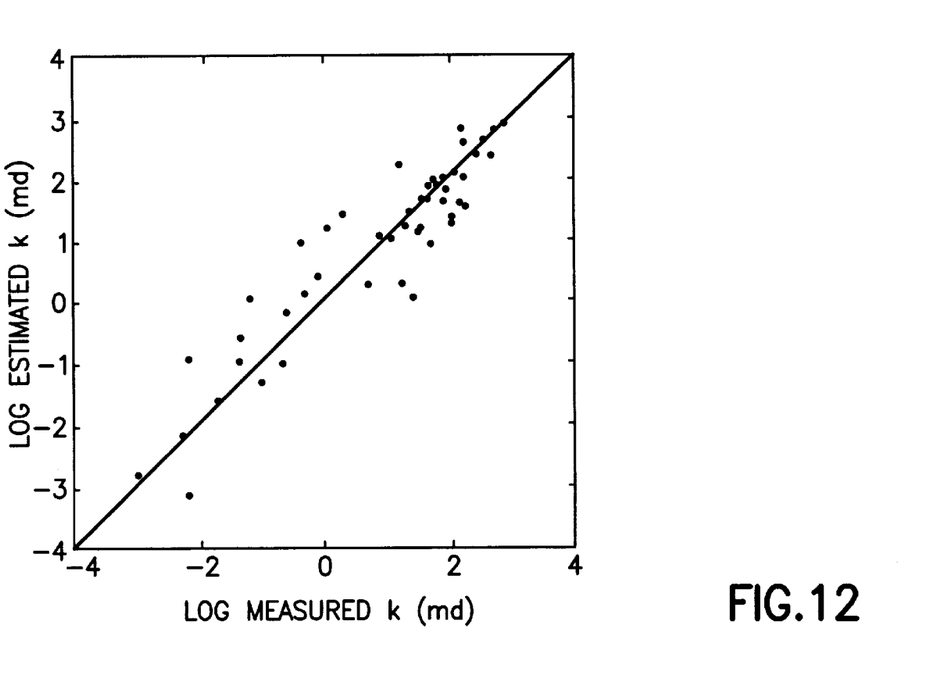
FIG. 12 shows another logarithm plot of measured permeability versus the logarithm of the complete k-Lambda estimate (Equations 15, 16) using the mineralogy data of Wendlandt and Bhuyan.

Referring to FIG. 12, the logarithm of measured permeability is compared with the k-Lambda estimate from Equations (15) and (16) using the porosity and mineralogy data of Wendlandt and Bhuyan. The value of m* was in Equation (12). The correlation coefficient for the log k values is 0.92.

Figure 13:
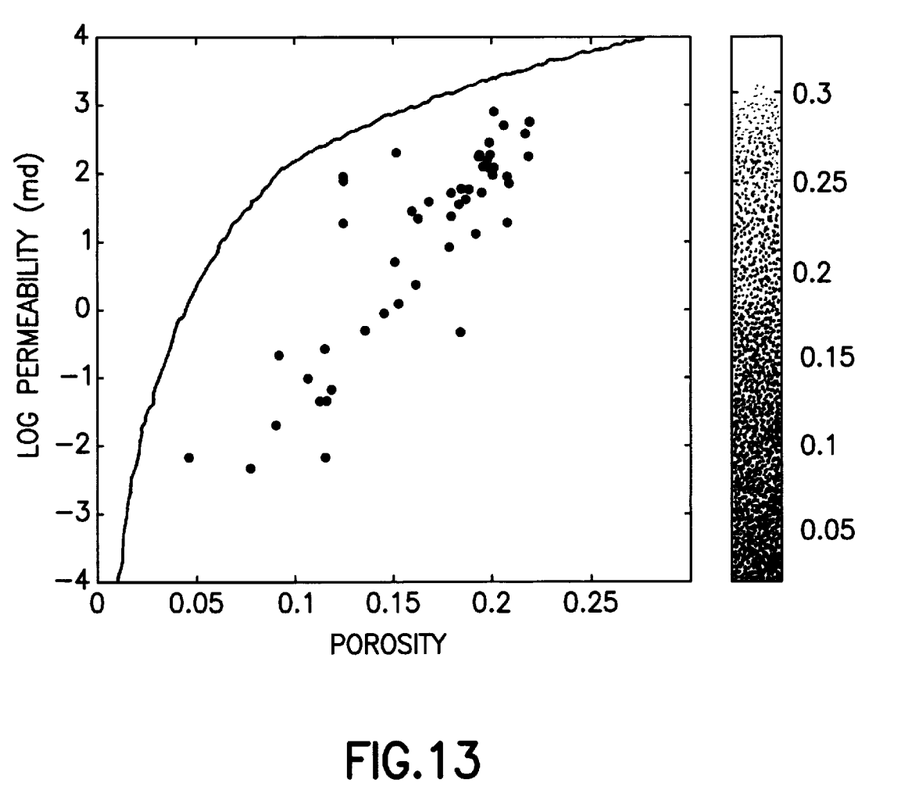
FIG. 13 illustrates a semi-logarithmic plot of core porosity and core permeability values for Utah Samples.

Referring to FIG. 13, the core porosity and permeability data are shown for the Utah samples in a conventional semilogarithmic poroperm plot. Unlike the Fontainebleau samples, the Utah samples show a fairly linear pattern that is often found in reservoir samples.

The near-linearity of the core data is due to the fact that samples with lower clay concentrations (lighter) have higher porosities and are closer to the clay-free line; samples with more clay (darker) have lower porosities and are further from the clay-free permeability.

Figure 14:
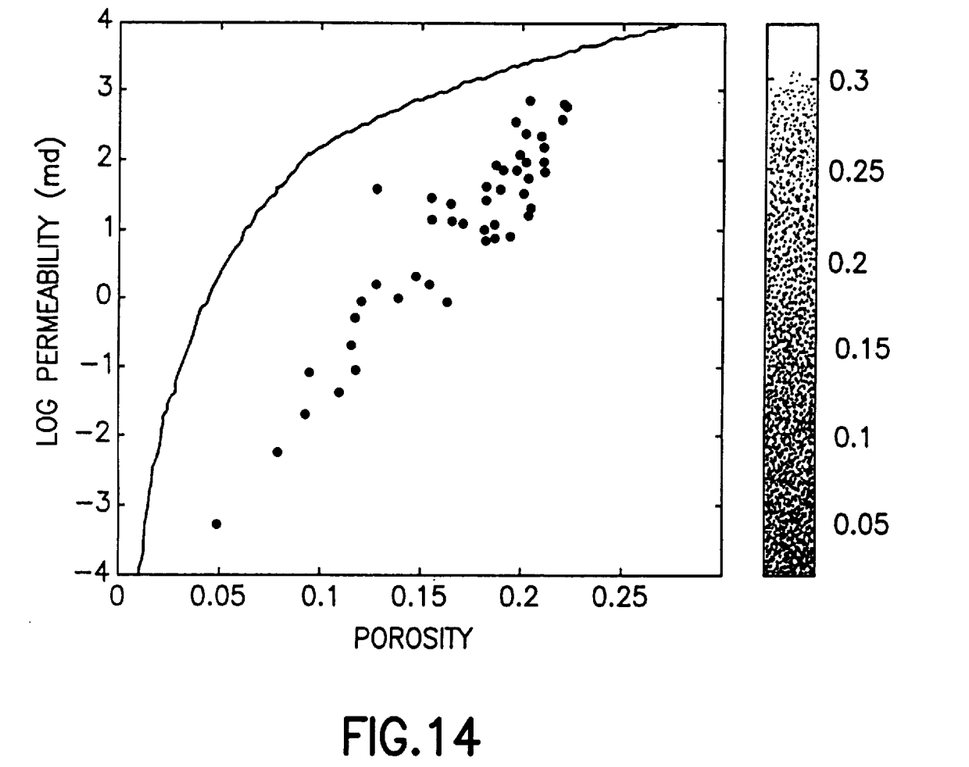
FIG. 14 depicts a semi-logarithmic plot of porosity and k-Lambda estimated permeability values for Utah Samples.

Referring to FIG. 14, the core porosity is illustrated, along with the k-Lambda permeability estimate, in a conventional poroperm plot. The near-linearity of the poroperm plot seen in FIG. 13 is even more pronounced when the k-Lambda permeability estimates are plotted.

A Mineral Form of k-Lambda Using Geochemical Logs

An important aspect of the k-Lambda approach is that it can be activated using log data. As discussed above, the NMR form of k-Lambda requires a total porosity and $T_1$ or $T_2$ data. The mineral form of k-Lambda is best activated with total porosity and estimates of the mineral fractions. The better the mineral estimates, the better the permeability estimate.

Figure 15:
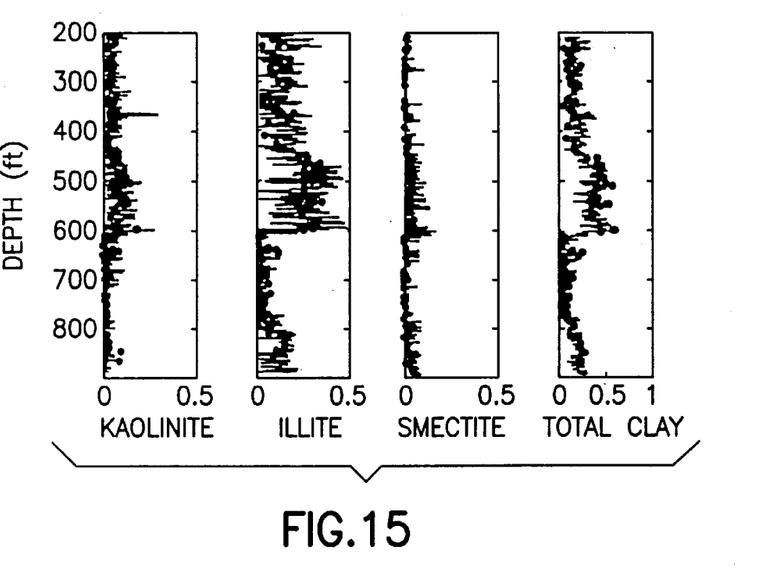
FIG. 15 shows graphic views of clay mineral concentrations for the Utah well of Wendlandt and Bhuyan determined by chemically-constrained X-ray diffraction, and mineral concentrations determined by default processing of Herron, S. L., Chiaramonte, J. M. and Herron, M. M., "Effect of Modifying Element Mineral Transforms on Geochemical Log Interpretation", Nuclear Geophysics (1994), 8(5), 411–432.

The best mineral estimates are made from geochemical log data. A Geochemical Logging Tool (GLT) was run in the same Utah well discussed above. The log data provides concentration logs for the chemical elements Al, Si, Ca, Fe, S, Ti, Gd, Th, U and K. Those elements are recomputed into concentration logs for the minerals kaolinite, illite, smectite, quartz, feldspar, dolomite, siderite and pyrite. The concentration logs for the clay minerals are shown in FIG. 15, along with the core mineral concentrations. It is apparent that the geochemical log data provide a means of estimating the individual clay minerals as well as the total clay with an accuracy heretofore not possible with conventional logs.

Figure 16:
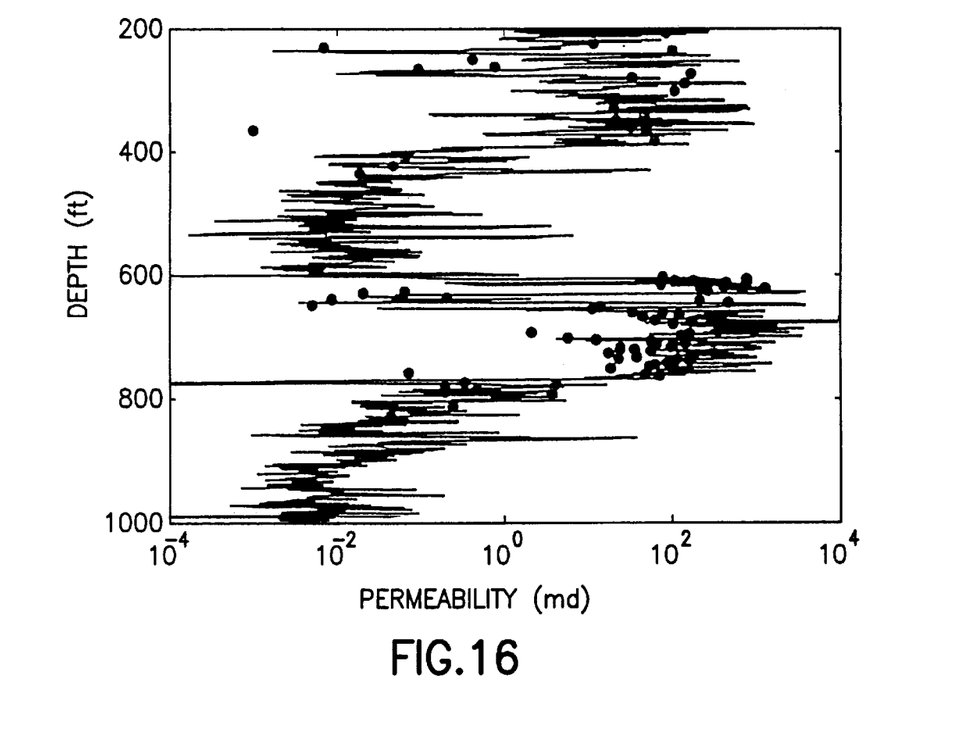
FIG. 16 illustrates a graphic view of measured permeability for the Utah well and the complete k-Lambda permeability estimate (Equations 15, 16) determined from total porosity and geochemical log mineral concentrations.

In FIG. 16, the mineralogy concentration logs and the total porosity log were combined using Equations (15) and (16) into a continuous k-Lambda permeability log. That estimate, with no adjustable parameters, compares very well to the discontinuous permeability values from the core plugs.

A Mineral Form of k-Lambda Using Conventional Logs

While the best mineral estimates are provided when geochemical log data are included, less accurate but still useful permeability estimates can be made in many cases from more conventional log data. The most important inputs are the total porosity, the amount of clay, and the type of clay. Frequently, the type of clay can be obtained as a local parameter. Alternatively, illite, the world's most commonly occurring clay, can be assumed to be the dominant local clay. Total porosity logs can be obtained from a variety of well-known logs. The best estimate for the total clay content, excluding geochemical data, would be from gamma ray, thorium, or neutron-density separation.

As part of a reservoir characterization effort to redevelop an old field in Venezuela, Bryant et al calculated k-Lambda from available old logs. They included the new FT-IR mineral analysis that showed that in the sands, the primary clays were equal parts of kaolinite and illite; while in the shales, significant smectite was also present. The clay content was mapped to the gamma ray using measured Th, U, and K concentrations on core. A k-Lambda permeability estimate has been computed from the specific surface area data in Table 1, along with the clay-from-gamma ray and a total porosity log.

Figure 17:
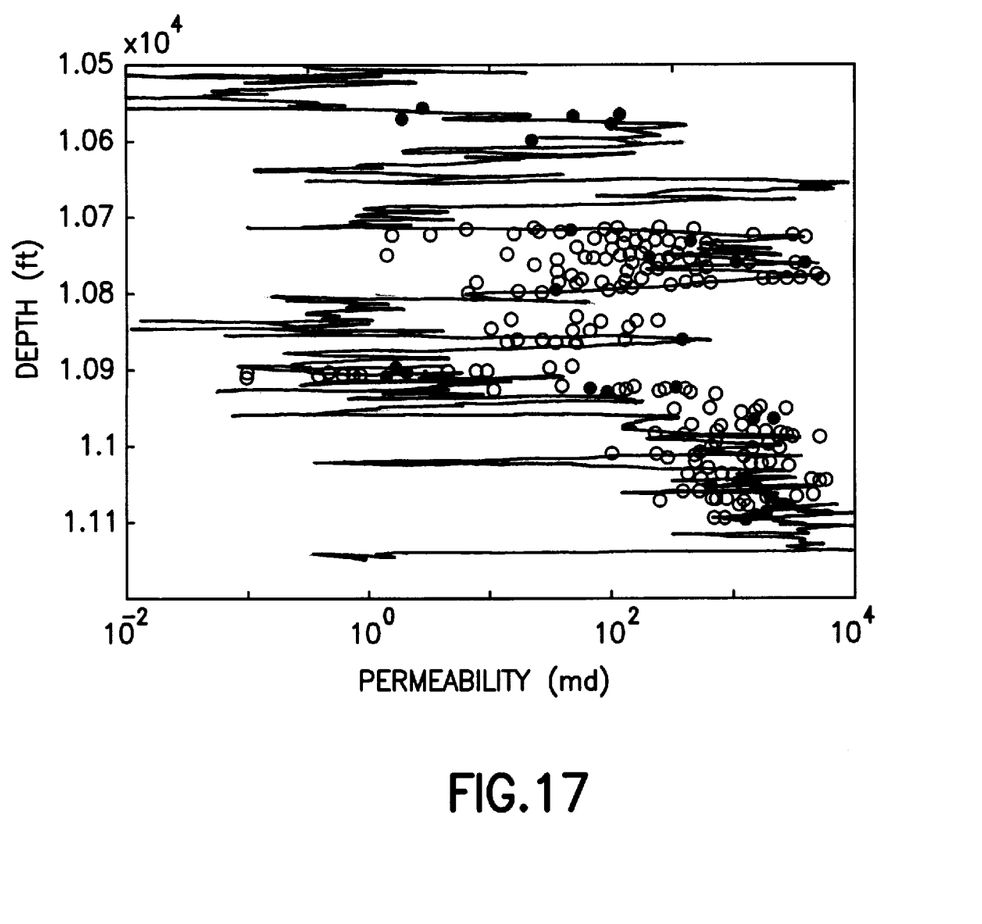
FIG. 17 depicts a graphic view of measured permeability for a Venezuela well described in Bryant, I. D., Baygun, B., Herron, M. M., Mattson, A., Ramamoorthy, R., Stewart, L., Tariq, S. M., Coll, M. C., Cordova, P., Gamero de Villarroel, H., Hernandez, L., Jiminez, Z., Leon, K. and Rondon, L., "Integration of Old and New Measurements to Optimize Redevelopment of the Lower Lagunillas Reservoir of Bloque IV, Lake Maracaibo, Venezuela", paper SPE 36096 presented at the Fourth Latin American and Caribbean Petroleum Engineering Conference, Port-of-Spain, Trinidad & Tobago, Apr. 23–26, 1996; and the k-Lambda estimate determined from bulk density and gamma ray logs.

Referring to FIG. 17, there is shown the full k-Lambda estimate along with decades old core measurements from two independent laboratories. While the mineral characterization from the gamma ray is less than ideal (see Herron, S. L. and Herron, M. M., "Quantitative Lithology: An Application for Open and Cased Hole Spectroscopy", Transactions of the 37th Annual Logging Symposium, SPWLA, Paper E, p. 14), the permeability log agreed well with the core data in this and three other wells in the field. The k-Lambda permeability was found to be useful in well-to-well correlation. Average values were used as input to the field simulator model.

The k-Lambda approach is a unifying model for estimating permeability in sedimentary rock from a variety of data sources. In simple pore systems at high porosity and permeability, the k-Lambda estimate is equivalent to the Kozeny-Carman equation. At lower porosities and permeabilities, the estimate is systematically lower than the Kozeny-Carman value due to progressively more severe pore blocking. For core data, the Sen et al permeabilities can be estimated from the measured specific surface areas or from the NMR $T_1$ data. For the Fontainebleau sandstones, the same approach worked exceedingly well with a mineral-based form of the k-Lambda model. For the mineralogically complex Utah sands and shaly sands, the same model gave very good results as long as the $v_i$ term for clays was set to 0.1.

For log data, the basic required inputs are total porosity, amount of clay, and type of clay. Type of clay can be externally supplied or illite or illite/kaolinite can be assumed. In lieu of geochemical data, total clay estimates and total porosities can be obtained from open hole wireline, cased hole wireline or LWD sources.

The k-Lambda methodology cannot be directly applied to all carbonate reservoirs, because of the importance of microporosity and the varied morphology of different mineral species.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A method of estimating permeability of a rock formation using a lambda parameter, $\Lambda$, representing the size of dynamically connected pores in said rock formation, said method comprising the steps of:
    a) obtaining core data for a rock formation;
    b) estimating permeability values for said rock formation from a first, k-Lambda expression and said core data, and when at least a portion of the permeability values derived from said first k-lambda expression does not correlate with measured permeability; then
    c) estimating said permeability of said rock formation using a second additional k-lambda expression for a portion of said core data to which said first k-lambda expression does not correlate.

2. The method of estimating rock formation permeability in accordance with claim 1, wherein said second alternative k-Lambda expression is represented by the general formula:

$$k_{\Lambda 2} = Z_2 \emptyset^{1.7m^*}/(S/V_p)^{3.4}$$

where:
    $k_{\Lambda 2}$ is a permeability value
    $\emptyset^{1.7m^*}$ is a pore factor related to the Archie formation factor, F, and $(S/V_p)^{3.4}$ is a surface area-to-pore volume ratio.

3. The method of estimating rock formation permeability in accordance with claim 1, wherein said data representative of said rock formation comprises core data, including pore size information.

4. The method of estimating rock formation permeability in accordance with claim 1, wherein said data representative of said rock formation comprises NMR information.

5. The method of estimating rock formation permeability in accordance with claim 1, wherein said data representative of said rock formation comprises mineral information.

6. The method of estimating rock formation permeability in accordance with claim 1, wherein said data representative of said rock formation comprises log data.

7. The method of estimating rock formation permeability in accordance with claim 1, wherein said data representative of said rock formation comprises seismic data.

8. The method of estimating rock formation permeability in accordance with claim 1, wherein said second k-lambda expression is generally applicable for pore sizes less than approximately 100 millidarcies.

9. A method of estimating permeability of a rock formation using a lambda parameter, $\Lambda$, representing the size of dynamically connected pores in said rock formation, said method comprising the steps of:
    a) obtaining core data for a rock formation;
    b) estimating permeability of said rock formation from a first, k-Lambda expression characterized by pore sizes exceeding a given threshold, and said core data, and when the permeability derived from said first k-lambda expression does not correlate with measured permeability for pore sizes less than said given threshold; then
    c) estimating said permeability of a portion of said rock formation using a second k-lambda expression characterized by pore sizes less than said given threshold.

10. The method of estimating rock formation permeability in accordance with claim 9, wherein said first k-lambda expression is generally applicable for pore sizes exceeding approximately 100 millidarcies.

11. A method of estimating permeability of a rock formation using a lambda parameter, $\Lambda$, representing the size of dynamically connected pores in said rock formation, said method comprising the steps of:
    a) determining whether a first k-Lambda estimate of permeability of said rock formation is greater or less than a predetermined quantity of millidarcies;
    b) estimating permeability of said rock formation from a first, k-Lambda expression if said estimate exceeds said predetermined quantity of millidarcies; and
    c) if less than said predetermined quantity; then estimating said permeability of said rock formation using a second, alternate k-Lambda expression.

12. The method of estimating rock formation permeability in accordance with claim 11, wherein said second alternative k-Lambda expression is represented by the general formula:

$$k_{\Lambda 2} = Z_2 \emptyset^{1.7m^*}/(S/V_p)^{3.4}$$

where:
    $k_{\Lambda 2}$ is a permeability value
    $\emptyset^{1.7m^*}$ is a pore factor related to the Archie formation factor, F, and $(S/V_p)^{3.4}$ is a surface area-to-pore volume ratio raised to the 3.4 power.

13. The method of estimating rock formation permeability in accordance with claim 11, wherein said determining step (a) is dependent upon data comprising pore size information.

14. The method of estimating rock formation permeability in accordance with claim 11, wherein said determining step (a) is dependent upon data comprising NMR information.

15. The method of estimating rock formation permeability in accordance with claim 11, wherein said determining step (a) is dependent upon data comprising log data.

16. The method of estimating rock formation permeability in accordance with claim 11, wherein said determining step (a) is dependent upon data comprising seismic data.

17. The method of estimating rock formation permeability in accordance with claim 11, wherein said predetermined quantity of millidarcies is approximately 100.

18. A method of estimating permeability of a rock formation using a lambda parameter, $\Lambda$, representing the size of dynamically connected pores in said rock formation, said method comprising the steps of:
    a) obtaining core data for a rock formation;
    b) determine whether surface-to-pore volume is greater or less than a threshold;
    c) estimating permeability of said rock formation from a first, k-Lambda expression when said surface-to-pore volume exceeds said threshold, and when less than said threshold; then
    d) estimating said permeability of said rock formation using a second k-lambda expression for said rock formation below said threshold.

19. The method of estimating rock formation permeability in accordance with claim 18, wherein said first k-lambda expression is generally applicable for pore sizes exceeding approximately 100 millidarcies.

20. The method of estimating rock formation permeability in accordance with claim 18, wherein said second k-lambda expression is generally applicable for pore sizes less than approximately 100 millidarcies.

* * * * *